(12) United States Patent
McKeny et al.

(10) Patent No.: US 8,275,740 B1
(45) Date of Patent: Sep. 25, 2012

(54) ELECTRONIC FORM DATA LINKAGE

(75) Inventors: Donald G. McKeny, Mesa, AZ (US); Jose Ramon Rosario, Phoenix, AZ (US)

(73) Assignee: Mardon E.D.P. Consultants, Inc., Mesa, AZ (US)

( * ) Notice: Subject to any disclaimer, the term of this patent is extended or adjusted under 35 U.S.C. 154(b) by 390 days.

(21) Appl. No.: 12/175,430

(22) Filed: Jul. 17, 2008

(51) Int. Cl.
*G06F 7/00* (2006.01)

(52) U.S. Cl. .................................................. 707/603

(58) Field of Classification Search .................. 707/603, 707/618, 602, 673

See application file for complete search history.

(56) References Cited

U.S. PATENT DOCUMENTS

| | | | |
|---|---|---|---|
| 7,171,615 | B2 | 1/2007 | Jensen et al. |
| 7,774,504 | B2 | 8/2010 | Chene et al. |
| 7,917,842 | B2 | 3/2011 | Garrison |
| 2004/0015778 | A1 | 1/2004 | Britton et al. |
| 2005/0027564 | A1 | 2/2005 | Yantis |
| 2005/0268217 | A1 | 12/2005 | Garrison |
| 2005/0289114 | A1 | 12/2005 | Bellamy |
| 2007/0168382 | A1* | 7/2007 | Tillberg et al. ............... 707/102 |
| 2008/0307298 | A1 | 12/2008 | Matveief et al. |

OTHER PUBLICATIONS

U.S. Appl No. 12/175,404: Application, filed Jul. 17, 2008, 51 pages.
U.S. Appl. No. 12/175,404: Filing Receipt and Notice to File Missing Parts, mailed Jul. 30, 2008, 5 pages.
U.S. Appl. No. 12/175,404: Notice to File Missing Parts Response, mailed Sep. 30, 2008, 7 pages.
U.S. Appl. No. 12/175,404: Filing Receipt, mailed Oct. 7, 2008, 3 pages.
U.S. Appl. No. 12/175,404: Non-Final Office Action, mailed Nov. 4, 2010, 19 pages.
U.S. Appl. No. 12/175,404: Non-Final Office Action Response, mailed Mar. 9, 2011, 21 pages.
U.S. Appl. No. 12/175,404: Final Office Action, mailed Mar. 25, 2011, 19 pages.
U.S. Appl. No. 12/175,404: Request for Continued Examination, mailed Aug. 25, 2011, 21 pages.
U.S. Appl. No. 12/175,404: Non-Final Office Action, mailed Sep. 27, 2011, 23 pages.
U.S. Appl. No. 12/175,404: Response to Non-Final OA and Interview summary, mailed Feb. 27, 2012, 24 pages.
U.S. Appl. No. 12/175,404: Notice of Allowance, mailed Mar. 20, 2012, 9 pages.
U.S. Appl. No. 12/175,417: Application, mailed Jul. 17, 2008, 55 pages.
U.S. Appl. No. 12/175,417: Filing Receipt and Notice to File Missing Parts, mailed Jul. 30, 2008, 5 pages.
U.S. Appl. No. 12/175,417: Notice to File Missing Parts Response, mailed Sep. 30, 2008, 7 pages.
U.S. Appl. No. 12/175,417: Filing Receipt, mailed Oct. 7, 2008, 3 pages.

(Continued)

*Primary Examiner* — Truong Vo

(74) *Attorney, Agent, or Firm* — Berkeley Law & Technology Group, LLP

(57) ABSTRACT

Subject matter disclosed herein may relate to electronic form processing systems and/or techniques, and may more particularly relate to data linkage for electronic forms. In one or more example embodiments, form data associated with one or more forms may be stored in a first database. The structures for one or more electronic forms may be defined, at least in part, by metadata stored in a second database. The one or more electronic forms may be generated based at least in part on the structures defined by the metadata from the second database and may be displayed using one or more subsets of the form data from the first database.

20 Claims, 9 Drawing Sheets

OTHER PUBLICATIONS

U.S. Appl. No. 12/175,417: Non-Final Office Action, mailed Oct. 4, 2011, 15 pages.
U.S. Appl. No. 12/175,417: Response to Non-Final Office Action, mailed Apr. 4, 2012, 22 pages.
U.S. Appl. No. 12/175,430: Application, filed Jul. 17, 2008, 57 pages.
U.S. Appl. No. 12/175,430: Filing Receipt and Notice to File Missing Parts, mailed Aug. 27, 2008, 5 pages.
U.S. Appl. No. 12/175,430: Notice to File Missing Parts Response, mailed Oct. 14, 2008, 12 pages.
U.S. Appl. No. 12/175,430: Filing Receipt, mailed Oct. 23, 2008, 3 pages.
U.S. Appl. No. 12/175,430: Non-Final Office Action, mailed Nov. 9, 2010, 14 pages.
U.S. Appl. No. 12/175,430: Non-Final Office Action Response, mailed Mar. 9, 2011, 15 pages.
U.S. Appl. No. 12/175,430: Notice to applicant regarding non-compliant Amendment, mailed Mar. 14, 2011, 2 pages.
U.S. Appl. No. 12/175,430: Abandonment, mailed Oct. 14, 2011, 2 pages.
U.S. Appl. No. 12/175,430: Petition for review by Office of Petitions, mailed Dec. 14, 2011, 21 pages.
U.S. Appl. No. 12/175,430: Notice to the applicant regarding a non-compliant amendment, mailed Feb. 14, 2012, 2 pages.
U.S. Appl. No. 12/175,430: Non-Final Office Action Response, mailed Apr. 16, 2012, 17 pages.

* cited by examiner

ELECTRONIC FORM DATA LINKAGE

This patent application is being concurrently filed with U.S. patent application Ser. No. 12/175,404, titled "Electronic Form Processing," filed on Jul. 17, 2008, by McKeny, et al.; and U.S. patent application Ser. No. 12/175,417, titled "Dynamic Loading of Library for Electronic Form Processing," filed on Jul. 17, 2008, by McKeny et al.; both of which are assigned to the assignee of currently claimed subject matter and incorporated by reference in their entirety.

FIELD

Subject matter disclosed herein may relate to electronic form processing systems and/or techniques, and may more particularly relate to data linkage for electronic forms.

BACKGROUND

Information gathering, record keeping, and information sharing are critical elements in a wide range of businesses, governments, and/or other organizations. Many businesses, governments, and/or other organizations have tremendous resources invested in forms printed on, or otherwise constructed from, paper. For example, in the medical field, patient information may be stored on paper forms to keep records of office visits, diagnoses, laboratory test results, medical histories, surgical notes, radiology reports, etc., to name but a few examples. Typically, in the healthcare field, a healthcare provider such as, for example, a doctor, nurse, and/or technician, may make written and/or printed (perhaps with a typewriter or a computer printer) entries onto an appropriate paper form for the given purpose. Such forms may have been developed over a period of time and modified and refined to serve specific, special purposes, and to meet the particular needs of a particular organization. Further, healthcare providers may acquire a good deal of experience in working with the forms, and may receive training in using the forms. The development, training, and experience acquired may represent a significant portion of the tremendous resources invested in the forms.

One difficulty that organizations may face in using paper forms to gather and store information is the difficulty in sharing the information both within a single organization and between different organizations. Other difficulties encountered may include the archiving and retrieval of information stored on paper forms. Accordingly, organizations are increasingly turning to electronic techniques and systems to gather and store information.

BRIEF DESCRIPTION OF THE FIGURES

Claimed subject matter is particularly pointed out and distinctly claimed in the concluding portion of the specification. However, both as to organization and/or method of operation, together with objects, features, and/or advantages thereof, it may best be understood by reference to the following detailed description when read with the accompanying drawings in which:

Figure 1:
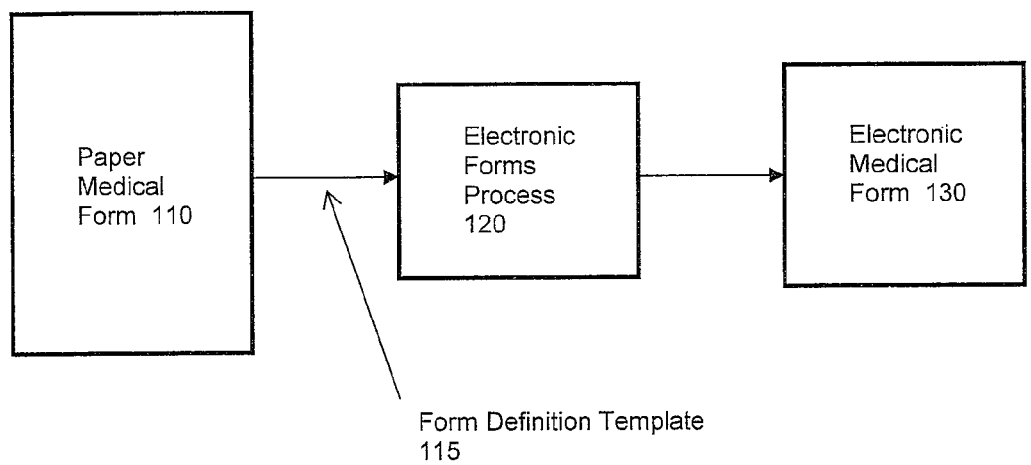
FIG. 1 is a block diagram of an example embodiment of an electronic form process.

Reference is made in the following detailed description to the accompanying drawings, which form a part hereof, wherein like numerals may designate like parts throughout to indicate corresponding or analogous elements. It will be appreciated that for simplicity and/or clarity of illustration, elements illustrated in the figures have not necessarily been drawn to scale. For example, the dimensions of some of the elements may be exaggerated relative to other elements for clarity. Further, it is to be understood that other embodiments may be utilized and structural and/or logical changes may be made without departing from the scope of claimed subject matter. It should also be noted that directions and references, for example, up, down, top, bottom, and so on, may be used to facilitate the discussion of the drawings and are not intended to restrict the application of claimed subject matter. Therefore, the following detailed description is not to be taken in a limiting sense and the scope of claimed subject matter defined by the appended claims and their equivalents.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, well-known methods, procedures, components and/or circuits have not been described in detail.

Embodiments claimed may include one or more apparatuses for performing the operations herein. These apparatuses may be specially constructed for the desired purposes, or they may comprise a general purpose computing platform selectively activated and/or reconfigured by a program stored in the device. The processes and/or displays presented herein are not inherently related to any particular computing platform and/or other apparatus. Various general purpose computing platforms may be used with programs in accordance with the teachings herein, or it may prove convenient to construct a more specialized computing platform to perform the desired method. The desired structure for a variety of these computing platforms will appear from the description below.

Embodiments claimed may include algorithms, programs and/or symbolic representations of operations on data bits or binary digital signals within a computer memory capable of performing one or more of the operations described herein. Although the scope of claimed subject matter is not limited in this respect, one embodiment may be in hardware, such as implemented to operate on a device or combination of devices, whereas another embodiment may be in software. Likewise, an embodiment may be implemented in firmware, or as any combination of hardware, software, and/or firmware, for example. These algorithmic descriptions and/or representations may include techniques used in the data processing arts to transfer the arrangement of a computing platform, such as a computer, a computing system, an electronic computing device, and/or other information handling system, to operate according to such programs, algorithms, and/or symbolic representations of operations. A program and/or process generally may be considered to be a self-consistent sequence of acts and/or operations leading to a desired result. These include physical manipulations of physical quantities. Usually, though not necessarily, these quantities take the form of electrical and/or magnetic signals capable of being stored, transferred, combined, compared, and/or otherwise manipulated. It has proven convenient at times, principally for reasons of common usage, to refer to these signals as bits, values, elements, symbols, characters, terms, numbers and/or the like. It should be understood, however, that all of these and/or similar terms are to be associated with the appropriate physical quantities and are merely convenient labels applied to these quantities. In addition, embodiments are not described with reference to any particular programming language. It will be appreciated that a variety of programming languages may be used to implement the teachings described herein.

Likewise, although the scope of claimed subject matter is not limited in this respect, one embodiment may comprise one or more articles, such as a storage medium or storage media. This storage media may have stored thereon instructions that if executed by a computing platform, such as a computer, a computing system, an electronic computing device, a cellular phone, a personal digital assistant, and/or other information handling system, for example, may result in an embodiment of a method in accordance with claimed subject matter being executed, for example. The terms "storage medium" and/or "storage media" as referred to herein relate to media capable of maintaining expressions which are perceivable by one or more machines. For example, a storage medium may comprise one or more storage devices for storing machine-readable instructions and/or information. Such storage devices may comprise any one of several media types including, but not limited to, any type of magnetic storage media, optical storage media, semiconductor storage media, disks, floppy disks, optical disks, CD-ROMs, magnetic-optical disks, read-only memories (ROMs), random access memories (RAMs), electrically programmable read-only memories (EPROMs), electrically erasable and/or programmable read-only memories (EEPROMs), flash memory, magnetic and/or optical cards, and/or any other type of media suitable for storing electronic instructions, and/or capable of being coupled to a system bus for a computing platform. However, these are merely examples of a storage medium, and the scope of claimed subject matter is not limited in this respect.

The term "instructions" as referred to herein relates to expressions which represent one or more logical operations. For example, instructions may be machine-readable by being interpretable by a machine for executing one or more operations on one or more data objects. However, this is merely an example of instructions, and the scope of claimed subject matter is not limited in this respect. In another example, instructions as referred to herein may relate to encoded commands which are executable by a processor having a command set that includes the encoded commands. Such an instruction may be encoded in the form of a machine language understood by the processor. For an embodiment, instructions may comprise run-time objects, such as, for example, Java and/or Javascript objects. However, these are merely examples of an instruction, and the scope of claimed subject matter is not limited in this respect.

Unless specifically stated otherwise, as apparent from the following discussion, it is appreciated that throughout this specification discussions utilizing terms such as processing, computing, calculating, selecting, forming, enabling, inhibiting, identifying, initiating, receiving, transmitting, determining, estimating, incorporating, adjusting, modeling, displaying, sorting, applying, varying, delivering, appending, making, presenting, distorting and/or the like refer to the actions and/or processes that may be performed by a computing platform, such as a computer, a computing system, an electronic computing device, and/or other information handling system, that manipulates and/or transforms data represented as physical electronic and/or magnetic quantities and/or other physical quantities within the computing platform's processors, memories, registers, and/or other information storage, transmission, reception and/or display devices. Further, unless specifically stated otherwise, processes described herein, with reference to flow diagrams or otherwise, may also be executed and/or controlled, in whole or in part, by such a computing platform.

Reference throughout this specification to "one embodiment" or "an embodiment" means that a particular feature, structure, or characteristic described in connection with the embodiment is included in at least one embodiment of claimed subject matter. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "and/or" as referred to herein may mean "and", it may mean "or", it may mean "exclusive-or", it may mean "one", it may mean "some, but not all", it may mean "neither", and/or it may mean "both", although the scope of claimed subject matter is not limited in this respect.

As discussed above, information gathering, record keeping, and information sharing are critical elements in a wide range of businesses, governments, and/or other organizations, and tremendous resources may be invested in paper forms. In the healthcare field, for example, patient information may be stored on paper forms to keep records of office visits, diagnoses, laboratory test results, medical histories, surgical notes, radiology reports, etc., to name but a few types of forms. As also mentioned previously, such paper forms may have been developed over a period of time and modified and refined to serve specific, special purposes, and to meet the particular needs of particular individuals and/or organizations. Users of such forms may acquire a good deal of experience in working with the forms, and may receive training in using the forms. The development, training, and experience acquired may represent a significant investment for these organizations.

As also discussed above, for a number of reasons, organizations may be increasingly turning to electronic techniques and systems to gather and store information. However, in turning to electronic systems, much of the investment in the paper forms may be lost. For example, personnel may need to be trained to use the electronic systems, and experience may be gained over a significant period of time before the personnel are able to reach the productivity levels previously achieved using the paper forms. Also, electronic systems may not be customized for each organization, and therefore various organization may be forced to alter procedures and/or processes in order to adapt to the electronic system. Therefore, it may be desirable to develop an electronic forms system that retains a significant amount of the investment made in the paper forms.

In general, for an example embodiment, an electronic form may be produced to maintain the approximate look and feel, or appearance, of a corresponding paper form. By producing an electronic form with the approximate appearance of a corresponding paper form, a user with prior experience working with the paper form may be able to readily utilize the electronic form. In this manner, previous training in using the paper form, as well as the previously acquired experience in using the paper form, may be transferred to the use of the electronic form. Similarly, by customizing electronic forms to visually match existing paper forms across an organization, the organization's practices and procedures may be largely maintained.

Many of the example embodiments described herein relate to the healthcare industry. Although these embodiments may find particular advantage in the healthcare industry, the scope of claimed subject matter is not limited in this respect, and embodiments are possible for use in any of a wide range of industries and/or applications.

As used herein, the term "form" is meant to include any document, whether hardcopy (paper) or electronic, on which entries may be made by an individual for the purposes of communicating, gathering, and/or storing information. One example of a form in the healthcare field may be a "medical history and examination form". A paper version of such a form may include numbered and/or labeled fields (spaces) for the patient's name, date of birth, sex, and address, for example. The form may also include fields for the recordation of vital signs, for an additional example. Also, the form may include fields for various body systems and/or organs, with checkboxes for "normal" and "abnormal" answers. The form may also include spaces for immunization information, and for test results, for further examples. Of course, this is merely an example form, and the scope of claimed subject matter is not limited in this respect.

FIG. 1 is a block diagram of an example embodiment of an electronic forms process. For this example, paper medical form 110 may be processed by electronic forms process 120 to produce an electronic medical form 130. For this example embodiment, consider the "medical history and examination" form mentioned above. This paper form may be processed by electronic forms process 120 to produce an electronic version 130 of the "medical history and examination" form. For this example, the electronic form 130 may maintain the approximate appearance of paper form 110. In maintaining the approximate appearance of paper form 110, electronic forms process 120 may create electronic form 130 with essentially all of the same numbered and/or lettered fields included on paper form 110. That is, for each numbered and/or labeled space on paper form 110, electronic form 130 may include a labeled and/or numbered field for data entry. Further, each of the fields on electronic form 110 may be located in approximately the same locations relative one to another as with the spaces on original paper form 110. That is, if the patient name field is located in the upper left hand corner of paper form 110, the patient name field of electronic form 130 may also be located in the upper left hand corner. Further, for one or more embodiments, the terminology used on paper form 110 may be maintained in electronic form 130. In this manner, a doctor or nurse familiar with paper form 110 may be able to readily utilize electronic form 130, without undue difficulties, and with minimal interruption of normal workflow and productivity.

For an embodiment, paper medical form 110 may be represented by a form definition template 115 that may serve as an input to electronic forms process 120. Template 115 may comprise information regarding paper medical form 110, such as, for example, the types and labels of fields on the form, the relative locations of the various fields, etc. For one embodiment, template 115 may be created by a human observing the characteristics of paper form 110 and determining which elements of paper form 110 would be desirable to maintain in electronic form 130. The form definition template may be generated manually for an embodiment. In another embodiment, the generation of the template may be accomplished via an automated process. For example, such an automated process may comprise a user drawing an image of the desired appearance of the electronic form on a computer screen utilizing some type of illustration tool to produce an image file, or the original paper form may be scanned by an imaging device to produce the image file. The image file may be automatically analyzed to generate a form definition template, for this example. However, these are merely examples of techniques for generating a form definition template, and the scope of claimed subject matter is not limited in this respect. Further, as used herein, the term "form definition template" is meant to include any technique and/or digital object, including but not limited to script files and/or other electronic documents, capable of specifying one or more characteristics of an electronic form.

For one example embodiment, form definition template 115 may comprise a Structured Query Language (SQL) script, although the scope of claimed subject matter is not limited in this respect. For example, the following SQL code segment may comprise at least a portion of a form definition template for an example "Respiratory Adult Triage Assessment" (RATA) form, including such fields as form_id, visit_id, physician_id, patient_name, etc. The depicted fields for this example represent a subset of the fields that might make up an RATA form for this example:

```
/* Check if table to be crated already exists, if so, then drop it */
DECLARE @ls_Buffer varchar(100)
SET nocount on
IF EXISTS ( SELECT * FROM sysobjects WHERE type = 'U' AND name = 'proFormRATA' )
BEGIN
    SELECT @ls_Buffer = 'Dropping table dbo.proFormRATA from the ' + rtrim( db_name( ) ) + ' database'
    PRINT @ls_Buffer
    DROP TABLE dbo.proFormRATA
END
SELECT @ls_Buffer = 'Installing table dbo.proFormRATA in the ' + rtrim( db_name( ) ) + ' database'
PRINT @ls_Buffer
go
/* Create table to store the EFP Respiratory Adult Triage Assessment Form information */
CREATE TABLE dbo.proFormRATA
(
        form_id                    varchar(25)            NOT NULL,
```

-continued

```
    visit_id                      varchar(25)         NOT NULL,
    mpi_id                        varchar(25)         NOT NULL,
    physician_id                  varchar(25)         NULL,
    patient_name                  varchar(100)        NULL,
    visit_number                  varchar(25)         NULL,
    birth_date                    datetime            NULL,
    age                           int                 NULL,
    start_service_date            datetime            NULL,
    sex                           char(1)             NULL,
    mr_number                     varchar(25)         NULL,
    physician_number              varchar(25)         NULL,
    form_date                     datetime            NULL,
    form_time                     datetime            NULL,
    diagnoses                     varchar(255)        NULL,
    initial_assessment            varchar(25)         NULL,
    follow_up_assessment          varchar(25)         NULL,
    chart_ps_minus_smoking_pts    bit                 NULL,
    chart_ps_plus_smoking_pts     bit                 NULL,
    chart_ps_chronic_resp_pts     bit                 NULL,
    chart_ps_pul_disease_pts      bit                 NULL,
    chart_ps_chronic_disease_pts  bit                 NULL,
    .
    .
    .
    vital_signs_hr                int                 NULL,
    vital_signs_rr                int                 NULL,
    vital_signs_bp                decimal             NULL,
    temp_24_hr_max                varchar(10)         NULL,
    .
    .
    .
    create_owner_id               int                 NOT NULL,
    create_user_id                int                 NOT NULL,
    create_date                   datetime            NOT NULL,
    create_station_id             integer             NOT NULL,
    modified_user_id              int                 NOT NULL,
    modified_date                 datetime            NOT NULL,
    modified_station_id           integer             NOT NULL
    constraint                    PK_RATA PRIMARY KEY (form_id)
--  constraint                    FK1_RATA FOREIGN KEY (create_user_id)
REFERENCES proUser(user_id),
--  constraint                    FK2_RATA FOREIGN KEY (create_station_id)
REFERENCES proStation(station_id),
--  constraint                    FK3_RATA FOREIGN KEY (modified_user_id)
REFERENCES proUser(user_id),
--  constraint                    FK4_RATA FOREIGN KEY (modified_station_id)
REFERENCES proStation(station_id)
);
GRANT INSERT, UPDATE, DELETE, SELECT ON proFormRATA TO profituser
```

Of course, the SQL code segment above is merely an example of a form definition template, and the scope of claimed subject matter is not limited in this respect. As previously mentioned, a form definition template in accordance with claimed subject matter may comprise any technique and/or process for defining one or more desired characteristics of the eventual electronic form.

For one or more embodiments, an electronic forms process may be performed to generate object-oriented code defining, at least in part, an electronic form based at least in part on a pre-existing paper form. The electronic forms process may receive a form definition template such as that described above, for example, and based at least in part on that template, may generate one or more object-oriented classes defining, at least in part, the electronic form. Object-oriented classes as they pertain to embodiments described herein are discussed more fully below.

Figure 2:
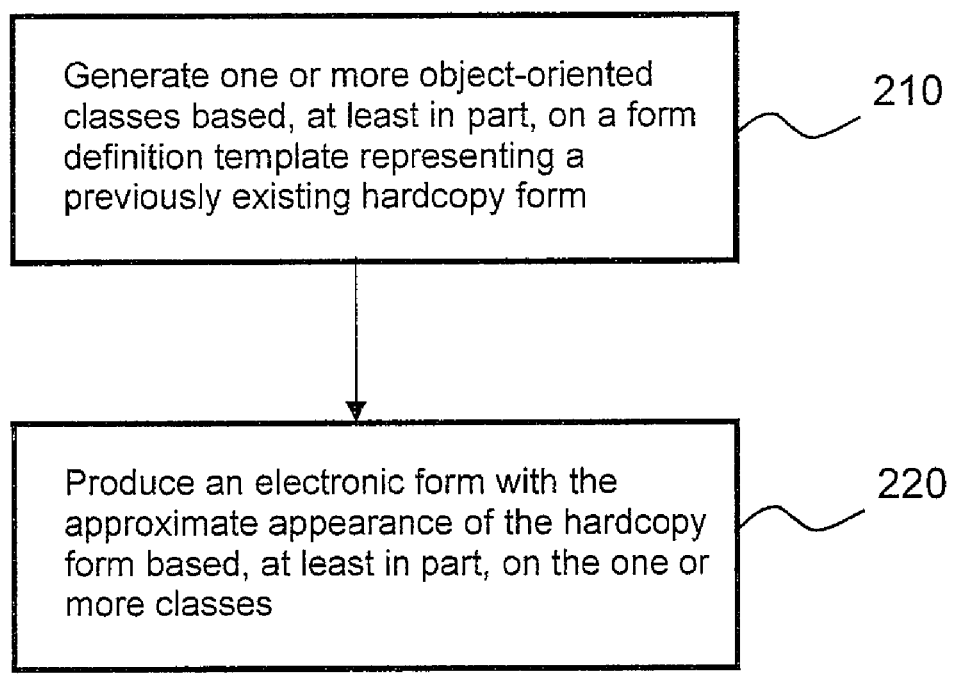
FIG. 2 is a flow diagram of an example embodiment of a method for producing an electronic form.

FIG. 2 is a flow diagram of an example embodiment of a method for producing an electronic form. At block 210, one or more object-oriented classes may be generated based, at least in part, on a form definition template representing a previously existing hardcopy (paper, for example) form. At block 220, an electronic form may be produced having the approximate appearance of the hardcopy form based, at least in part, on the one or more generated object-oriented classes. Of course, this is merely an example process for producing electronic forms. Example processes in accordance with claimed subject matter may include all, more than all, or less than all of blocks 210-220, and the scope of claimed subject matter is not limited in this respect.

In object-oriented programming, a class may be considered to define abstract characteristics of an object, including, for example, the object's attributes, fields, and/or properties, as well as the object's behaviors. For one or more embodiments, an electronic forms process may generate a plurality of classes based at least in part on the form definition template. For example, a form record class may be generated. The record class may define the characteristics of the various data elements on a form, for example. As another example, a form table class may be generated. The table class may represent an abstraction of a collection of records for a form.

A form control class may also be generated. For this example, the control class may comprise an abstraction of the form image, as well as define logic associated with the form. For example, the control class may comprise abstractions of operations that may be performed on a form, such as, for example, adding, deleting, updating, and/or querying data from the form. Also, the control class may include customizations to the form such as, for example, pull down menus for one or more data fields. Further, for this example, a form screen class may be generated. The screen class for this example may comprise an abstraction of the portion of a display viewable by a user. That is, the screen class may define at least in part the view or views observable by a user. A screen class may comprise a single form, or may comprise a plurality of forms for one or more embodiments.

The various classes generated in this example may be compiled, that is, compiled classes may be placed into one or more libraries. Libraries as they relate to embodiments described herein are discussed more fully below.

Figure 3:
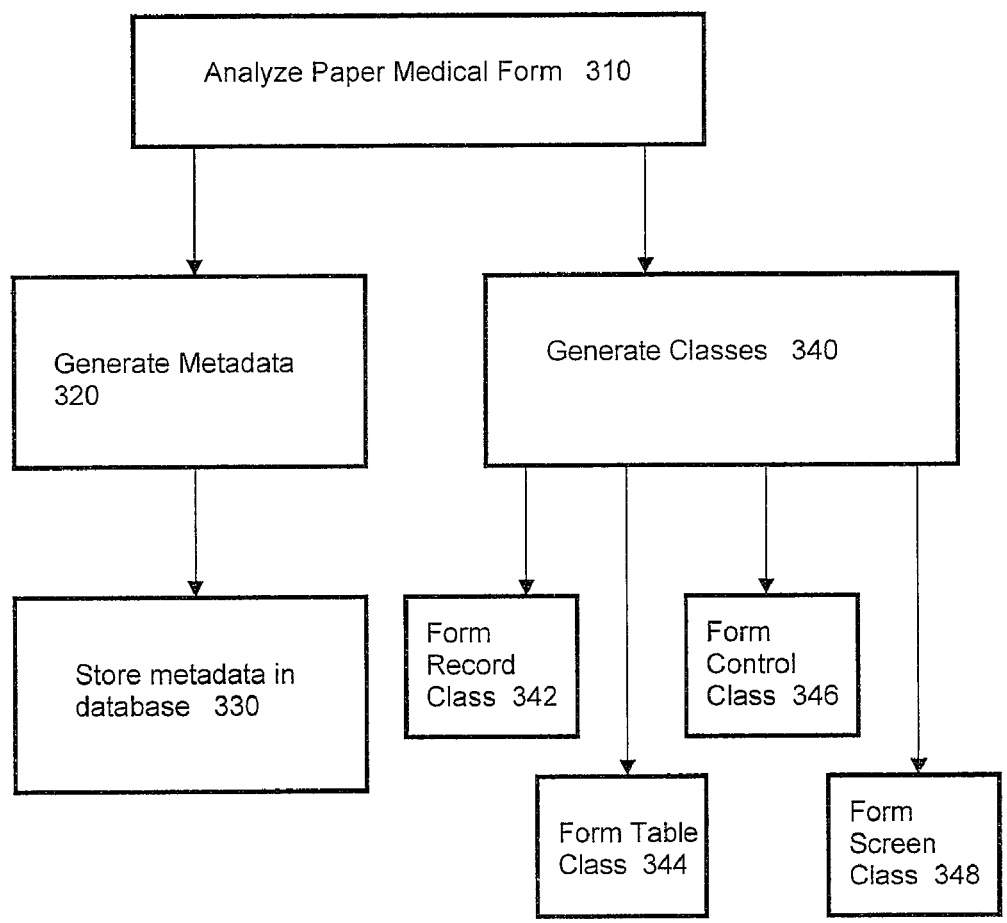
FIG. 3 is a block diagram of an example embodiment of an electronic form process.

FIG. 3 is a block diagram of an example embodiment of an electronic form process. At block 310, a paper medical form may be analyzed, perhaps as described above either by a human and/or by an automated process. At block 340, various object-oriented classes may be generated according to the example process described above. For this example, a form record class 342 may be generated, as well as a form table class 344, a form control class 346, and a form screen class 348. Of course, these are merely examples of the types of classes that may be generated, and the scope of claimed subject matter is not limited in this respect. As described above, the generated classes may define various characteristics of an electronic form. Also as described above, the electronic form may be designed to maintain an approximate appearance of the original paper form in order to leverage previous investments in the paper form.

For this example, as part of the electronic forms process generating the electronic form, metadata may be produced at block 320 and stored in a database at block 330. In general, the generated metadata may describe form field names, may describe which fields belong to which forms, and further may describe which form is contained in which library, and/or where the library is stored, for example. Metadata as it relates to embodiments described herein is further discussed below.

Figure 4:
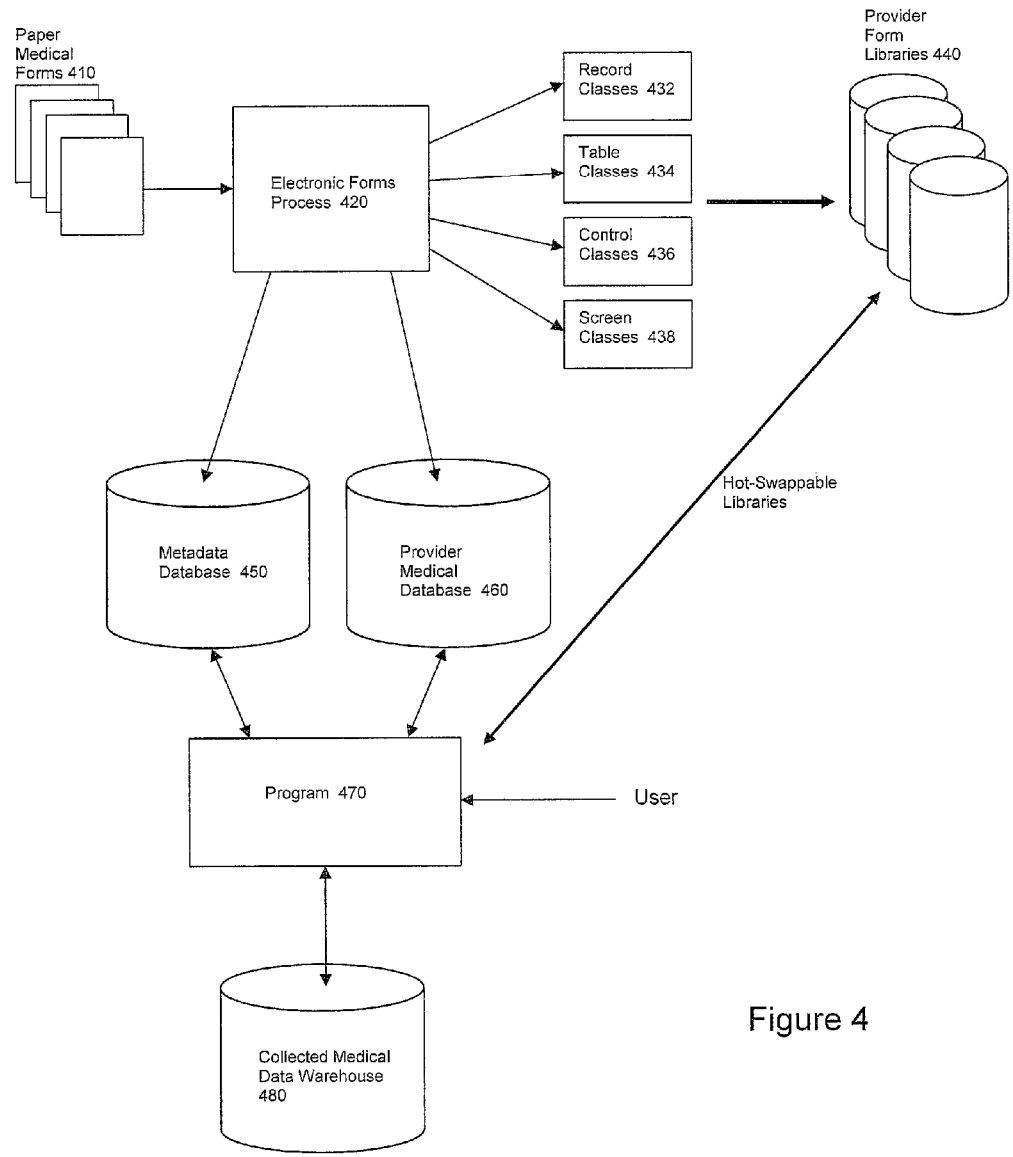
FIG. 4 is a block diagram of an example embodiment of an electronic form processing and information storage system.

FIG. 4 is a block diagram of an example embodiment of an electronic form processing and information storage system 400. System 400 may comprise one or more of the elements of the example embodiments previously described in connection with FIGS. 1-3. For example, paper medical forms 400 may be processed by an electronic forms process 420 to produce one or more record classes 432, one or more table classes 434, one or more control classes 436, and one or more screen classes 438. Upon instantiation, that is, if the classes are compiled, the compiled classes may be stored in one or more libraries 440. For this example embodiment, each of libraries 440 may represent a library associated with a particular organization, such as, for example, a healthcare provider. As such, libraries 440 for this example may be referred to as provider form libraries.

For this example embodiment, paper medical forms 410 may comprise any of a very wide range of possible form types. Further, forms 410 may comprise a collection of forms from a single particular organization, or may comprise collections of forms from across multiple organizations. Forms from differing organizations may be processed separately for one embodiment, and the resulting processed electronic forms may be stored in organization-specific libraries. Also for one or more embodiments, forms from differing organizations may be customized according to each organization's existing paper forms, and/or according to each organization's particular needs. System 400 may also provide a greater ease of sharing data from one organization to another, while still maintaining each organization's customized data collection solutions. The sharing of data between organizations is discussed more fully below.

For this example embodiment, system 400 may comprise a metadata database 450 and a provider medical database 460. Metadata database 450 may contain metadata produced by electronic forms process 420. As described previously, such metadata may comprise information describing form field names, information relating fields to forms, and information relating forms to libraries, for example. The metadata may also describe the location of particular libraries, for another example. Provider medical database 460 may contain various support data pertaining to forms that are specific to a particular healthcare provider. Patient medical information generated by a healthcare provider may be stored in a collected medical data warehouse 480, discussed more fully below. The patient medical information may comprise data entries for a number of fields of a number of forms. For this example embodiment, provider medical database 460 may be accessible only by a single healthcare provider, and by no other organization. Also for this example, a healthcare provider may only access its own libraries, and may be denied access to libraries provided for other organizations. Security measures may be put in place to safeguard the patient's medical information, although the scope of claimed subject matter is not limited in this respect.

Further, for this example embodiment, a program 470 may be performed on a computing platform. Such a program may direct the computing platform to perform any of a wide range of applications. In the medical field, possible applications may include, but are not limited to, retrieving previously gathered patient information (medical history), and/or inputting new and/or additional patient information. The user of such a program may be a doctor, nurse, and/or technician, for example. For one or more embodiments, the user may be a patient. Of course, these are merely example types of applications and users, and the scope of claimed subject matter is not limited in this respect.

To retrieve a patient's medical history, for an example, program 470 may access metadata database 450 to determine which library to load in order to be able to bring up the appropriate form or forms, and may access provider medical database 460 to retrieve support data specific to the particular healthcare provider for the form or forms defined by the loaded library. For one or more embodiments, the support data specific to the particular healthcare provider may include, but is not limited to, relatively static and/or completely static information, such as, for example, a patient master index, patient addresses, specialized medical terms utilized by the healthcare provider, information to allow conversions between standardized medical terms and customized terms utilized by the healthcare provider, etc. To further retrieve the patient's medical history for this example, the metadata may be read by program 470 to determine which library to dynamically load, and which data to display. Patient data entries may be retrieved from collected medical data warehouse 480 and displayed in the form or forms, for this example. Thus, the stored patient data, support data, and metadata, along with the library, may enable program 470 to display a form containing patient data to the user.

For this example embodiment, a library may comprise compiled code, derived from the generated classes described above, and may be loaded by an operating system at run-time. One possible advantage of the library architecture described herein is the ability to make modifications to a library, perhaps as forms are created and/or modified, in the background without the user of program 470 being aware (unless, or course, visual changes are made to one or more forms that may catch the user's attention). The user, therefore, may be assured of utilizing the most recent versions of the forms without having taken any action of his/her own. In this manner, the maintenance and creation of forms may be accomplished without intervention by the user. Similarly, if changes are needed for a form, or if a new form is created, there is no need to update or recompile program 470, but rather the library may be updated and/or a new library may be generated to replace the previous library.

For example system 400, program 470 may comprise a program executed locally on a computing platform comprising one or more of a desktop computer, notebook computer, tablet computer, personal digital assistant, cellular telephone, etc. Of course, these are merely examples of computing platform types, and the scope of claimed subject matter is not limited in this respect. In another embodiment, program 470 may be executed on a remote computer that may be accessed by a local computing platform via the Internet, for example, or via some other type of network.

System 400 for this example may also comprise collected medical data warehouse 480, as discussed above. Data warehouse 480 may contain patient medical information entries, and may contain copies of at least some information contained in databases 450 and/or 460, for one or more embodiments. As described previously, for this example embodiment database 460, which may contain support data for one or more forms pertaining to a particular healthcare provider, may be accessed only by a single healthcare provider organization. However, for one or more embodiments, more than one organization may gain access to data warehouse 480, which may contain patient medical information entries. Access to data warehouse 480 and to specific information contained in warehouse 480 may be restricted to those organizations having proper permissions to access the information. Possible types of organizations that may access information in data warehouse 480 are discussed below in connection with FIG. 8.

For one or more embodiments, if a form is to be edited by a user, the form is generated as described above by retrieving metadata from metadata database 450, loading an appropriate provider form library 440 based on the metadata, and by loading form support data from the provider medical database 460. In one or more examples, form data may be retrieved from collected medical data warehouse 480. The form data may comprise patient medical data, for this example. The user may view the electronic form, based on a previously existing paper form, and may add additional patient information, and/or may modify and/or delete previously existing information. The modified form data, comprising, for this example, patient medical data, may be stored in the collected medical data warehouse. Thus, if a user inputs or modifies patient medical data, that data may be stored in the collected medical warehouse. In some embodiments, some patient data may also be stored in the provider medical database, although the scope of claimed subject matter is not limited in this respect.

Figure 5:
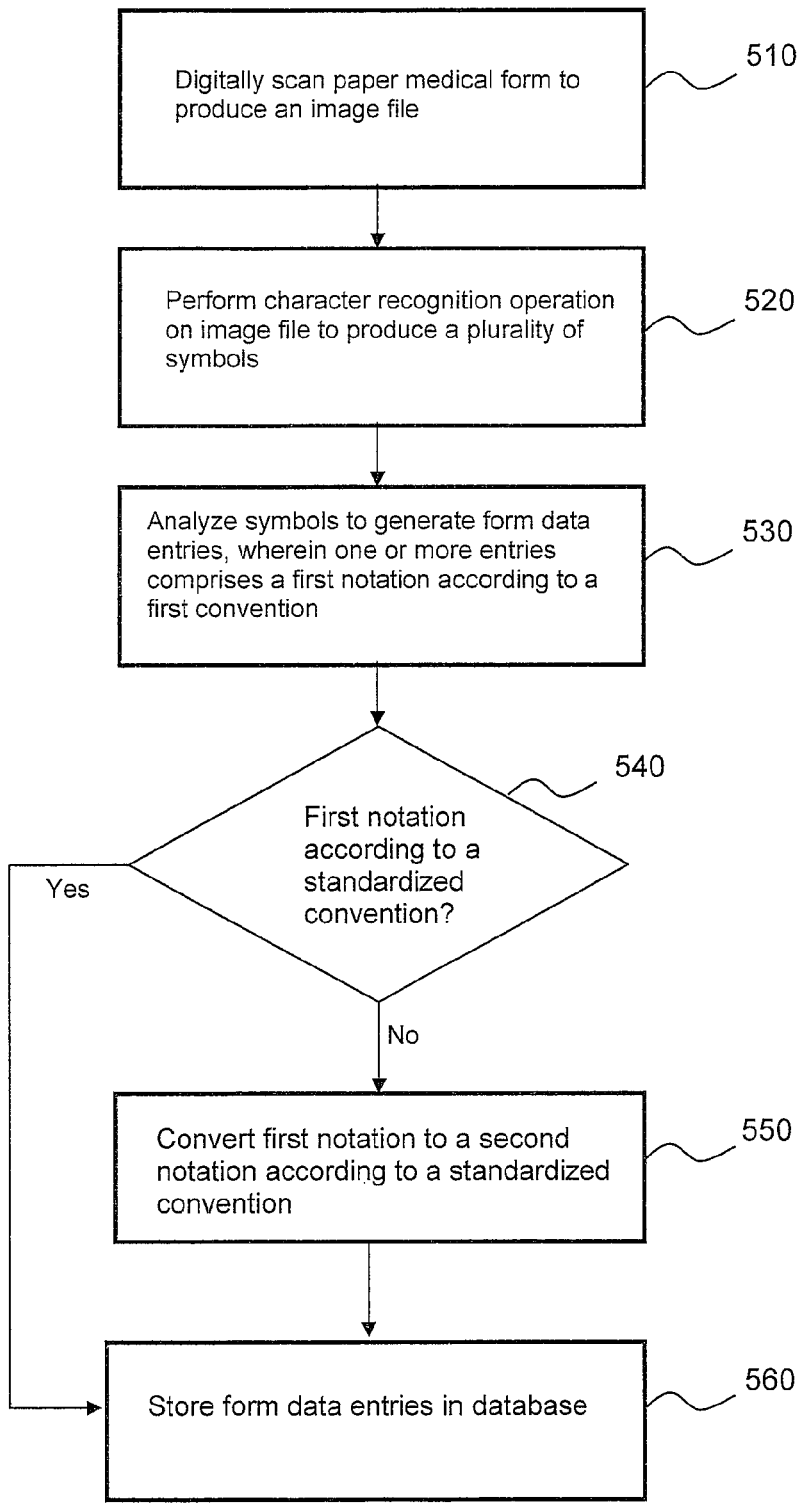
FIG. 5 is a flow diagram of an example embodiment of a method for gathering information from a paper form.

FIG. 5 is a flow diagram of an example embodiment of a method for gathering information from a paper form. If an organization such as a healthcare organization implements an electronic form process, it may begin gathering new patient medical information on the generated electronic forms. However, such an organization may desire to glean patient medical histories from older paper forms, and have those histories stored in an electronic format as with the more recent data. The flow diagram of FIG. 5 depicts an example embodiment of a process for gathering information from a previously existing and notated paper form. At block 510, a paper medical form may be digitally scanned to produce an image file, and at block 520 character recognition operations may be performed over the image file to produce a number of symbols that may represent text and/or numbers and/or other symbol types. At block 530, the symbols may be analyzed in order to generate data entries for an electronic form corresponding to the previously existing paper form. For this example, one or more entries may be notated according to a first convention. For example, in the medical field there may be a number of ways to notate blood glucose levels, for just one example. In order to make it easier for an organization to share information within that organization or with other organizations, it may be advantageous for system 400, for example, to understand the different ways to notate blood glucose levels, and to store such entries according to a standardized convention. Therefore, for this example, at block 540, a determination may be made as to whether the first notation complies with the standardized convention. If the notation is compliant, the data entries may be stored in a database at block 560. However, if the notation is not according to the standardized convention, the first notation may be converted to the standard convention at block 550. For one or more embodiments, in order to maintain customized forms and also to enable easier sharing of information, the data entries may be stored in a data warehouse accessible to more than one organization according to the standardized convention, thereby allowing other organizations to view the stored data entries and understand the information contained therein. Also, the data entries stored on the organization's proprietary database, such as, for example, database 460 discussed above, may be stored according to the healthcare provider's original convention. However, these are merely examples of storing data according to various notation conventions, and the scope of claimed subject matter is not limited in these respects.

Figure 6:
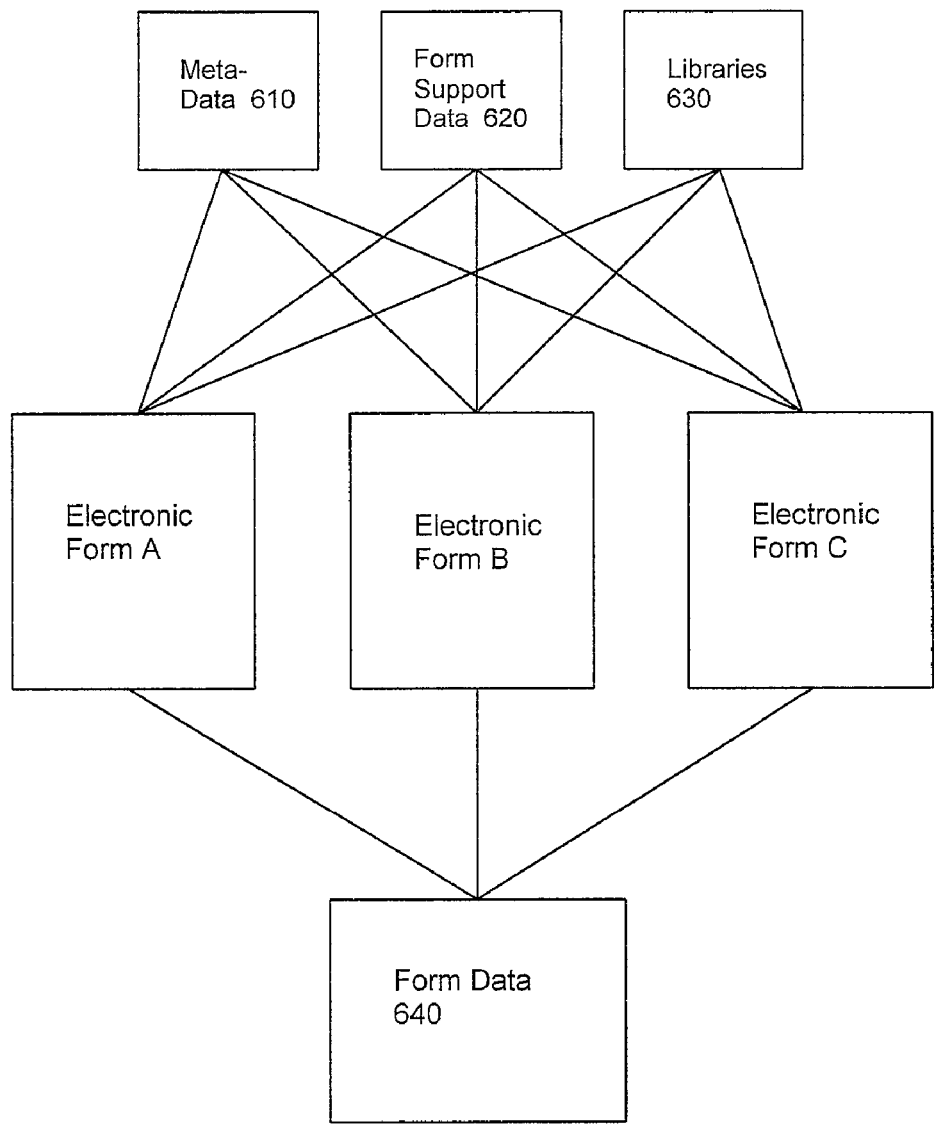
FIG. 6 is a block diagram illustrating an example embodiment of data relationships among a number of electronic forms.

FIG. 6 is a block diagram illustrating data linkage relationships among a number of electronic forms. For this example, three electronic forms A, B, and C are shown, although the scope of claimed subject matter is not limited in this respect. For this example embodiment, the electronic forms represent forms that may be electronically displayed to a user with the approximate appearance of previously existing hardcopy forms, although again, the scope of claimed subject matter is not limited in this respect. Electronic forms A, B, and C may be defined, at least in part, by metadata 610, form support data 620, and/or libraries 630. For example, metadata 610 may include location information for one or more of libraries 630, and libraries 630 may comprise a plurality of object-oriented classes associated with one or more of electronic forms A, B, and C, and may define, at least in part, the structure or organization of the electronic forms. Form data 640 may be stored in a central database, referred to in one or more embodiments as a collected form data database, and may provide form data for each of electronic forms A, B, and C, for example. Thus, entries in form data 640 may be linked to or otherwise associated with more than one form. In this manner, there is no need for separate databases for each of the electronic forms, and the electronic forms may share a pool of data. Of course, electronic forms A, B, and C may not include the same data entries, but rather may include different subsets of form data 640.

By providing a mechanism by which electronic forms may share a source for form data, if an entry in the form data is modified, the modified entry may be automatically reflected in whichever electronic forms are associated with that particular modified entry. Thus, as electronic forms are generated for display at the request of a user, the electronic form may be assured of gathering up-to-date form data. This is in contrast to a situation where the form data for the various electronic forms is stored in separate databases, with no data linkage, and where information for one form may be up-to-date, but the corresponding information for another electronic form may be out-of-date.

The data linkage configuration described above, as well as configurations for other example embodiments, is made possible by separating the form data from the electronic form image. That is, the form data is not stored as an image file, but is rather stored, for one or more examples, as data to be displayed according to electronic form definitions provided by the metadata and/or libraries, as described above.

Figure 7:
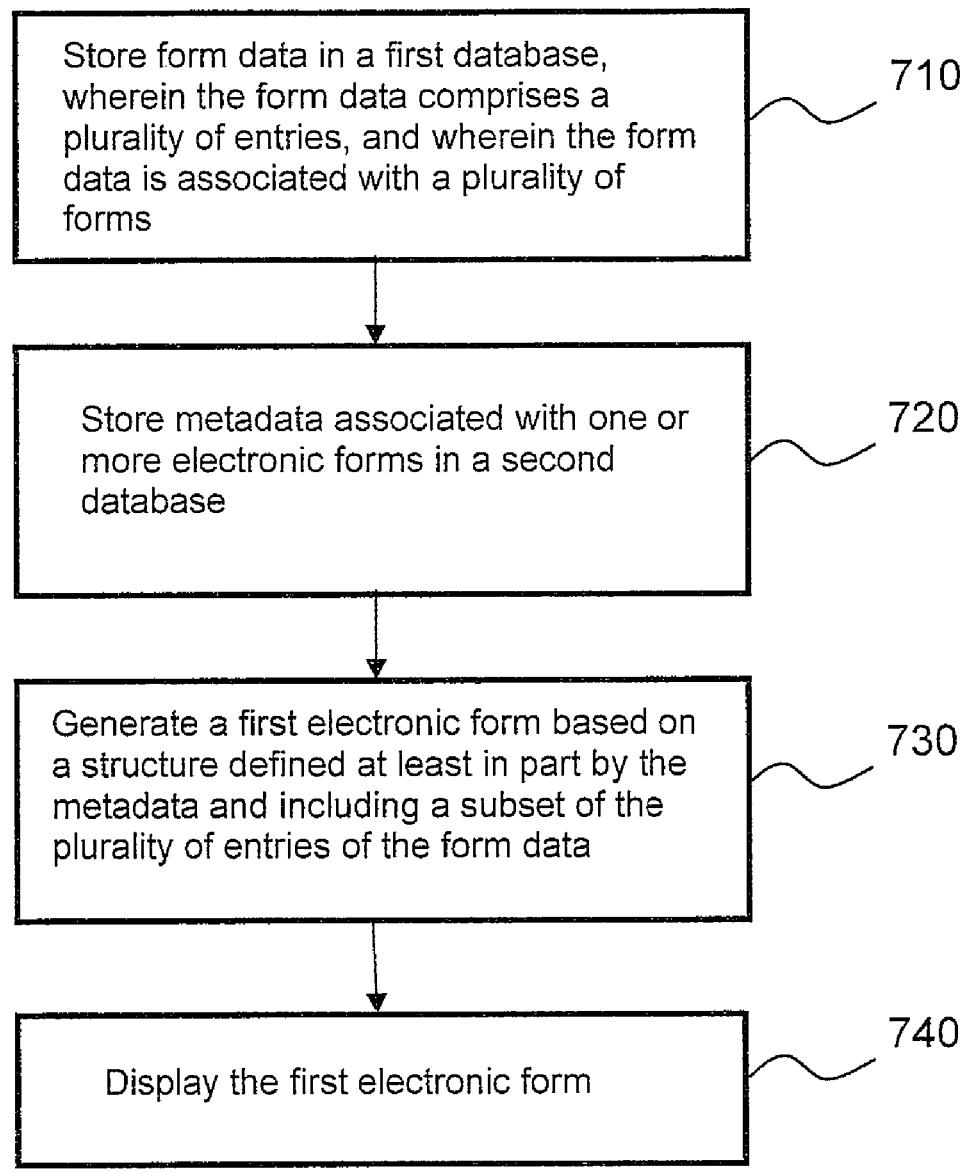
FIG. 7 is a flow diagram of an example embodiment of a method for generating an electronic form using metadata from one database and form data from another database.

FIG. 7 is a flow diagram of an example embodiment of a method for generating an electronic form using metadata from one database and form data from another database, according to the data linkage embodiments described above. At block 710, form data may be stored in a first database. The form data may comprise a plurality of entries, and the form data may be associated with a plurality of forms. At block 720, metadata associated with one or more electronic forms may be stored in a second database. At block 730, a first electronic form may be generated based on a structure defined, at least in part, by the metadata and including a subset of the plurality of entries of the form data. At block 740, the electronic form may be displayed. Embodiments in accordance with claimed subject matter may include less than, or more than, or all of blocks 710-740. Further, the order of blocks 710-740 is merely an example order, and the scope of claimed subject matter is not limited in this respect.

Expanding on the example embodiment depicted in FIG. 7, form support data associated with one or more electronic forms may be stored in a third database. The first electronic form may be generated based, at least in part, on at least a subset of the form support data, for an example embodiment. Also, a second electronic form may be generated based on a second structure defined at least in part by the metadata and including a second plurality of entries of the form data. For one or more embodiments, the first and second subsets of form data may include at least some entries in common, although the scope of claimed subject matter is not limited in this respect.

In one or more embodiments, the metadata may include a location of a first library associated with at least the first electronic form, wherein the first library may include one or more object-oriented classes that may define, at least in part, the first structure. The first electronic form may be generated based, at least in part, on the first structure defined at least in part by the first library. Similarly, for an example embodiment, the first library may further include one or more object-oriented classes that may define, at least in part, the second structure. The second electronic form may be generated based, at least in part, on the second structure defined at least in part by the first library, although the scope of claimed subject matter is not limited in this respect.

Further, for one or more embodiments, the one or more object-oriented classes of the first library may represent a first previously existing hardcopy form. Also, the first electronic form may be displayed with an approximate appearance of the first previously existing hardcopy form, although again, the scope of claimed subject matter is not limited in this respect. For one or more embodiments, the previously existing hardcopy form may comprise a paper medical form, and the first electronic form may comprise an electronic medical form. For this example, the form data may comprise patient medical information, although the scope of claimed subject matter is not limited in this respect.

Figure 8:
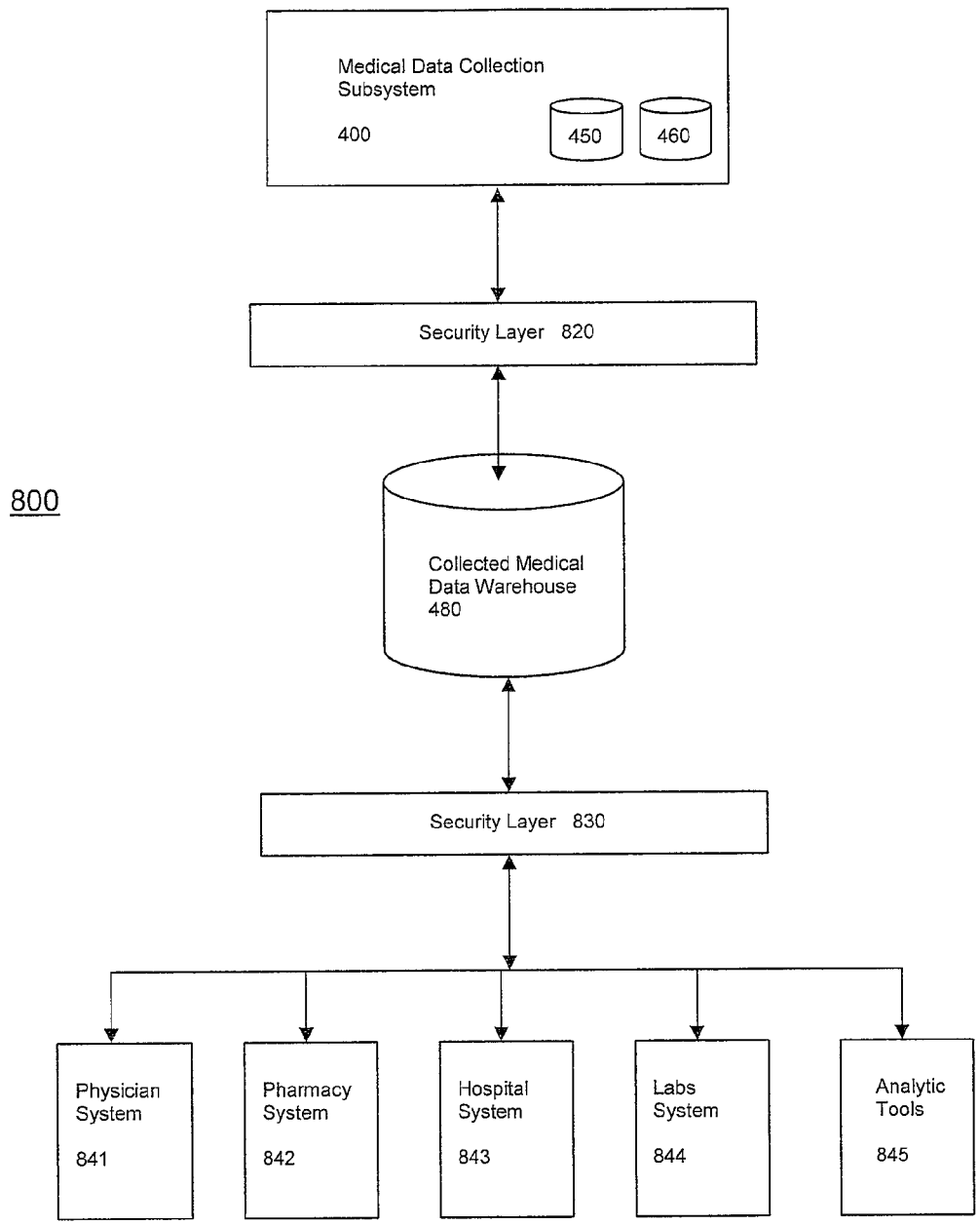
FIG. 8 is a block diagram of an example embodiment of an information storage system.

FIG. 8 is a block diagram of an example embodiment of an information storage system 800. System 800 for this example may comprise a medical data collection subsystem 400, including databases 450 and 460. Subsystem 400 and databases 450 and 460 may comprise the example system 400 described above in connection with FIG. 4. Also included in system 800 is collected medical data warehouse 480, previously described in connection with FIG. 4, above. System 800 for this example may further comprise a number of different entities associated with the healthcare industry. Of course, these are merely examples of the types of entities and/or organizations that may belong to such a system, and the scope of claimed subject matter is not limited in these respects. For this example embodiment, system 800 may comprise a physician subsystem 841, a pharmacy system 842, a hospital system 843, a laboratory system (labs) 844, and an analytic tools system 845. Physician system 841 is meant to denote any physician or other medical services provider that may have legitimate desires to access patient medical records stored in collected medical data warehouse 480. Similarly, pharmacy system 842 may represent any pharmacist or pharmacy organization with legitimate desires to access patient medical records stored in warehouse 480. In like fashion, hospital system 843 and labs system 844 are meant to denote any hospital facility or laboratory facility, respectively, with legitimate desires to access patient medical records. For this system, collected medical data warehouse 480 may contain the collected medical records of any or all of the various systems of system 800. In this manner, the various systems may be able to readily exchange information. For this example embodiment, security layers 820 and 830 may help to ensure that only authorized entities gain access to appropriate patient medical records.

One difficulty that many organizations may face in exchanging medical records with other organizations is the lack of standards for record keeping. For example, each organization may have its own peculiar form structures and/or notation conventions. Thus, problems may arise if the different organizations use non-standard forms or non-standard terminologies. As one simple example, consider that some healthcare organizations may notate an oral glucose tolerance test "OGTT" while other organizations may notate this test simply as "GTT". While this may seem to be a small, simple difference, nevertheless this difference may prevent one organization from accurately sharing patient information with another organization. Similar problems may also exist on an intra-organizational basis if the organization lacks a standard notation convention.

Of course, one solution to the problem of mismatched naming conventions would be to have each organization adhere to a standard notation convention, and to a standard set of forms. However, as previously mentioned, a great number of organizations have tremendous resources invested in current systems, and the costs in terms of money and loss of productivity would be immense. Also, each organization would need to agree on the standard convention, which may have little hope of succeeding. Therefore, the techniques described above in the various example embodiments may be advantageous in solving these difficulties. As described above, each organization may have its own set of forms and its own notation conventions. Patient data for some embodiments may be stored within a particular organization in that organization's proprietary form and notation format, and/or may also be stored in a central data warehouse using a standard notation convention. As information is shuttled from one organization to another through the central data warehouse, notation conversions may be made in order to ensure accurate communication of the information.

For an embodiment, system 400 may further comprise analytic tools system 845. Analytic tools system 845 for this example may represent any technique for analyzing patient medical records stored in collected medical data warehouse 480. With patient medical records stored in a central location in a standardized format, a myriad of possibilities may exist for analyzing the patient medical records. Of course, system 800 is merely an example system, with an example collection of interconnected healthcare provider systems, and the scope of claimed subject matter is not limited in these respects. A wide range of other embodiments are possible with other system configurations.

Figure 9:
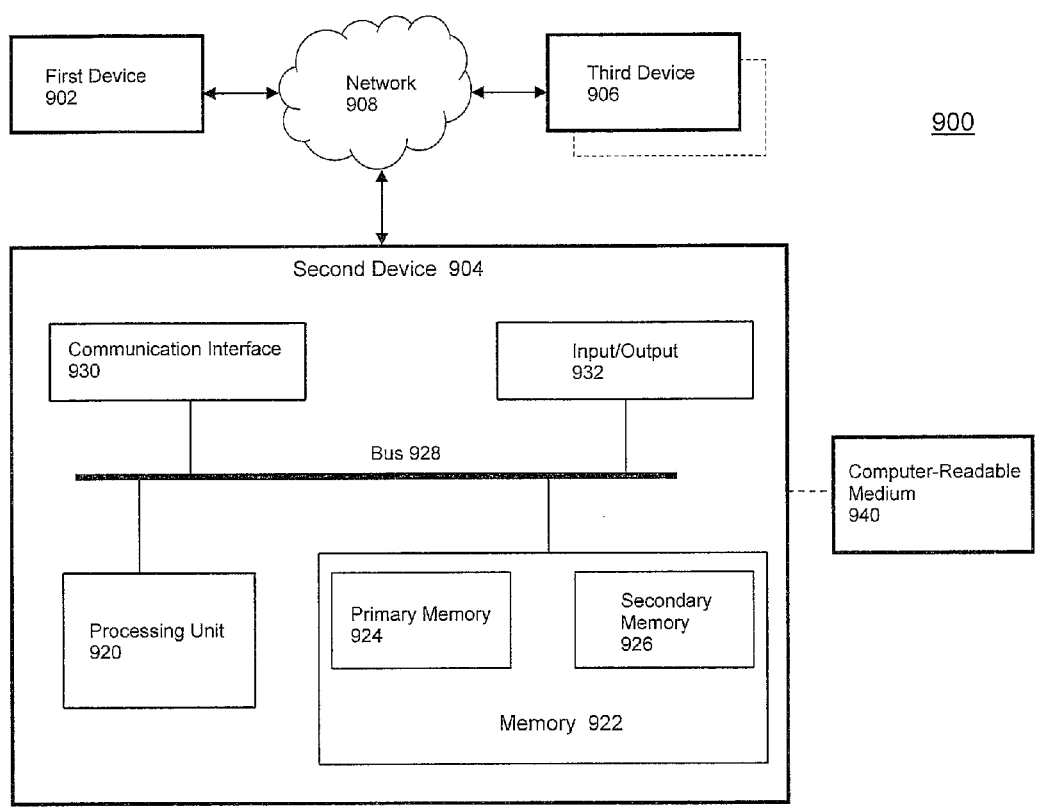
FIG. 9 is a block diagram of an example embodiment of a computing system.

FIG. 9 is a schematic diagram illustrating an exemplary embodiment of a computing environment system 900 that may include one or more devices adapted to perform electronic forms processing using one or more of the techniques discussed above in connection with FIGS. 1-8, for example. System 900 may include, for example, a first device 902, a second device 904, and a third device 906, which may be operatively coupled together through a network 908.

First device 902, second device 904 and third device 906, as shown in FIG. 9, may be representative of any device, appliance or machine that may be adapted to exchange data over network 908. By way of example but not limitation, any of first device 902, second device 904, or third device 906 may include: one or more computing devices and/or platforms, such as, e.g., a desktop computer, a laptop computer, a workstation, a server device, or the like; one or more personal computing or communication devices or appliances, such as, e.g., a personal digital assistant, mobile communication device, cellular phone, or the like; a computing system and/or associated service provider capability, such as, e.g., a database or data storage service provider/system, a network service provider/system, an Internet or intranet service provider/system, a portal and/or search engine service provider/system, a wireless communication service provider/system; and/or any combination thereof.

Similarly, network 908, as shown in FIG. 9, is representative of one or more communication links, processes, and/or resources configurable to support the exchange of data between at least two of first device 902, second device 904, and third device 906. By way of example but not limitation, network 908 may include wireless and/or wired communication links, telephone or telecommunications systems, data buses or channels, optical fibers, terrestrial or satellite resources, local area networks, wide area networks, intranets, the Internet, routers or switches, and the like, or any combination thereof. As illustrated, for example, by the dashed lined box illustrated as being partially obscured of third device 906, there may be additional like devices operatively coupled to network 908.

It is recognized that all or part of the various devices and networks shown in system 900, and the processes and methods as further described herein, may be implemented using or otherwise include hardware, firmware, software, or any combination thereof.

Thus, by way of example but not limitation, second device 904 may include at least one processing unit 920 that is operatively coupled to a memory 922 through a bus 928.

Processing unit 920 is representative of one or more circuits configurable to perform at least a portion of a data computing procedure or process such as, for example the electronic forms processes described above in connection with FIGS. 1-8. By way of example but not limitation, processing unit 920 may include one or more processors, controllers, microprocessors, microcontrollers, application specific integrated circuits, digital signal processors, programmable logic devices, field programmable gate arrays, and the like, or any combination thereof.

Memory 922 is representative of any data storage mechanism. Memory 922 may include, for example, a primary memory 924 and/or a secondary memory 926. Primary memory 924 may include, for example, a random access memory, read only memory, etc. While illustrated in this example as being separate from processing unit 920, it should be understood that all or part of primary memory 924 may be provided within or otherwise co-located/coupled with processing unit 920.

Secondary memory 926 may include, for example, the same or similar type of memory as primary memory and/or one or more data storage devices or systems, such as, for example, a disk drive, an optical disc drive, a tape drive, a solid state memory drive, etc. In certain implementations, secondary memory 926 may be operatively receptive of, or otherwise configurable to couple to, a computer-readable medium 940. Computer-readable medium 940 may include, for example, any medium that can carry and/or make accessible data, code and/or instructions for one or more of the devices in system 900.

Second device 904 may include, for example, a communication interface 930 that provides for or otherwise supports the operative coupling of second device 904 to at least network 908. By way of example but not limitation, communication interface 930 may include a network interface device or card, a modem, a router, a switch, a transceiver, and the like.

Second device 904 may include, for example, an input/output 932. Input/output 932 is representative of one or more devices or features that may be configurable to accept or otherwise introduce human and/or machine inputs, and/or one or more devices or features that may be configurable to deliver or otherwise provide for human and/or machine outputs. By way of example but not limitation, input/output device 932 may include an operatively configured display, speaker, keyboard, mouse, trackball, touch screen, data port, etc.

It should also be understood that, although particular embodiments have just been described, the claimed subject matter is not limited in scope to a particular embodiment or implementation. For example, one embodiment may be in hardware, such as implemented to operate on a device or combination of devices, for example, whereas another embodiment may be in software. Likewise, an embodiment may be implemented in firmware, or as any combination of hardware, software, and/or firmware, for'example. Such software and/or firmware may be expressed as machine-readable instructions which are executable by a processor. Likewise, although the claimed subject matter is not limited in scope in this respect, one embodiment may comprise one or more articles, such as a storage medium or storage media. This storage media, such as one or more CD-ROMs and/or disks, for example, may have stored thereon instructions, that when executed by a system, such as a computer system, computing platform, or other system, for example, may result in an embodiment of a method in accordance with the claimed subject matter being executed, such as one of the embodiments previously described, for example. As one potential example, a computing platform may include one or more processing units or processors, one or more input/output devices, such as a display, a keyboard and/or a mouse, and/or one or more memories, such as static random access memory, dynamic random access memory, flash memory, and/or a hard drive, although, again, the claimed subject matter is not limited in scope to this example.

In the preceding description, various aspects of claimed subject matter have been described. For purposes of explanation, specific numbers, systems and/or configurations were set forth to provide a thorough understanding of claimed subject matter. However, it should be apparent to one skilled in the art having the benefit of this disclosure that claimed subject matter may be practiced without the specific details. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all such modifications and/or changes as fall within the true spirit of claimed subject matter.

What is claimed is:

1. A method, comprising:
    storing one or more form entries comprising a plurality of records in a first database in a memory of a computing system accessible by a first provider organization;
    storing one or more object-oriented classes specifying one or more characteristics of one or more electronic forms in the memory of the computing system accessible by the first provider organization;
    displaying a first electronic form of the one or more electronic forms in accordance with one or more characteristics indicated by the one or more object-oriented classes stored in the memory of the computing system accessible by the first provider organization, wherein the first electronic form is populated at least in part with a first subset of the plurality of records stored in the first database, wherein the first subset of the plurality of records stored in the first database is reflective at least in part of information provided by a centralized database accessible by the first provider organization, wherein the centralized database is further accessible by one or more additional provider organizations, wherein the one or more object-oriented classes comprise logic associated with one or more respective fields of the first electronic form to perform one or more operations on the subset of the plurality of records stored in the first database at least in part in response to displaying the electronic form; and
    securing the one or more object-oriented classes and the first subset of the plurality of records stored in the first database against access from the one or more additional provider organizations.

2. The method of claim 1, further comprising storing form support data associated with the one or more electronic forms in a third database accessible by the first provider organization, wherein said displaying the first electronic form comprises displaying the first electronic form based, at least in part, on at least a subset of the form support data.

3. The method of claim 2, further comprising displaying a second electronic form in accordance with the one or more object-oriented classes, wherein the second electronic form is populated at least in part with a second subset of the plurality of records stored in the first database.

4. The method of claim 3, wherein the first subset of records and the second subset of records include at least some records in common.

5. The method of claim 4, further comprising:
    compiling the one or more object-oriented classes to generate a respective one or more instantiated classes;
    storing the one or more instantiated classes in a first library in the memory of the computing platform; and
    generating metadata indicating a location of the first library.

6. The method of claim 5, wherein said displaying the second electronic form comprises displaying the second electronic form in accordance with one or more additional characteristics indicated at least in part by the one or more object-oriented classes of the first library.

7. The method of claim 5, wherein the one or more object-oriented classes of the first library represent one or more previously existing hardcopy forms, and wherein said displaying the first electronic form comprises displaying the first electronic form with an approximate appearance of a first previously existing hardcopy form of the one or more previously existing forms.

8. The method of claim 7, wherein the first previously existing hardcopy form comprises a paper medical form, wherein the first electronic form comprises a first electronic medical form, and wherein the plurality of records of form entries comprise patient medical information.

9. The method of clam 8, wherein the centralized database comprises patient information for one or more patients.

10. An article, comprising: a non-transitory storage medium, having stored thereon instructions executable by a processor of a computing platform to:
    store one or more form entries comprising a plurality of records in a first database in a memory of the computing platform accessible by a first provider organization;
    store one or more object-oriented classes specifying one or more characteristics of one or more electronic forms in the memory of the computing platform accessible by the first provider organization;
    display a first electronic form of the one or more electronic forms in accordance with one or more characteristics indicated by the one or more object-oriented classes stored in the memory of the computing platform accessible by the first provider organization, wherein the first electronic form is populated at least in part with a first subset of the plurality of records stored in the first database, wherein the first subset of the plurality of records stored in the first database is reflective at least in part of information provided by a centralized database accessible by the first provider organization, wherein the centralized database is further accessible by one or more additional provider organizations, wherein the one or more object-oriented classes comprise logic associated with one or more respective fields of the first electronic form to perform one or more operations on the subset of the plurality of records stored in the first database at least in part in response to displaying the electronic form; and
    secure the one or more object-oriented classes and the first subset of the plurality of records stored in the first database against access from the one or more additional provider organizations.

11. The article of claim 10, wherein the storage medium has stored thereon further instructions executable by the processor of the computing platform to store form support data associated with the one or more electronic forms in a third database accessible by the first provider organization to and to display the first electronic form based, at least in part, on at least a subset of the form support data.

12. The article of claim 11, wherein the storage medium has stored thereon further instructions executable by the processor of the computing platform to display a second electronic form in accordance with the one or more object-oriented classes, wherein the second electronic form is populated at least in part with a second subset of the plurality of records stored in the first database.

13. The article of claim 12, wherein the first subset of records and the second subset of records include at least some records in common.

14. The article of claim 13, wherein the storage medium has stored thereon further instructions executable by the processor of the computing platform to:
compile the one or more object-oriented classes to generate a respective one or more instantiated classes;
store the one or more instantiated classes in a first library in the memory of the computing platform; and
generate metadata indicating a location of the first library.

15. The article of claim 14, wherein the storage medium has stored thereon further instructions executable by the processor of the computing platform to display the second electronic form at least in part by displaying the second electronic form in accordance with one or more additional characteristics indicated at least in part by the one or more object-oriented classes of the first library.

16. The article of claim 14, wherein the one or more object-oriented classes of the first library represent one or more previously existing hardcopy forms, and wherein the storage medium has stored thereon further instructions executable by the processor of the computing platform to display the first electronic form at least in part by displaying the first electronic form with an approximate appearance of a first previously existing hardcopy form of the one or more previously existing forms.

17. The article of claim 16, wherein the first previously existing hardcopy form comprises a paper medical form, wherein the first electronic form comprises a first electronic medical form, and wherein the plurality of records of form entries comprise patient medical information.

18. The article of clam 17, wherein the centralized database comprises a collected medical data warehouse, and wherein the form patient information for one or more patients.

19. An apparatus, comprising:
a processor to:
store one or more form entries comprising a plurality of records in a first database in a memory accessible by a first provider organization;
store one or more object-oriented classes specifying one or more characteristics of one or more electronic forms the memory accessible by the first provider organization;
display a first electronic form of the one or more electronic forms in accordance with one or more characteristics indicated by the one or more object-oriented classes stored in the memory accessible by the first provider organization, wherein the first electronic form is populated at least in part with a first subset of the plurality of records stored in the first database, wherein the first subset of the plurality of records stored in the first database is reflective at least in part of information provided by a centralized database accessible by the first provider organization, wherein the centralized database is further accessible by one or more additional provider organizations, wherein the one or more object-oriented classes comprise logic associated with one or more respective fields of the first electronic form to perform one or more operations on the subset of the plurality of records stored in the first database at least in part in response to displaying the electronic form; and
secure the one or more object-oriented classes and the first subset of the plurality of records stored in the first database against access from the one or more additional provider organizations.

20. The apparatus of claim 19, wherein the first electronic form comprises a first electronic medical form with an approximate appearance of a previously existing paper medical form, wherein the centralized database comprises patient information for one or more patients.

* * * * *